(12) United States Patent
Zeligs

(10) Patent No.: US 7,384,971 B2
(45) Date of Patent: *Jun. 10, 2008

(54) PHYTOCHEMICALS FOR THE TREATMENT OF CERVICAL DYSPLASIA

(75) Inventor: Michael A. Zeligs, Boulder, CO (US)

(73) Assignee: BioResponse L.L.C., Boulder, CO (US)

( * ) Notice: Subject to any disclaimer, the term of this patent is extended or adjusted under 35 U.S.C. 154(b) by 571 days.

This patent is subject to a terminal disclaimer.

(21) Appl. No.: 10/616,477

(22) Filed: Jul. 9, 2003

(65) Prior Publication Data

US 2004/0072891 A1    Apr. 15, 2004

Related U.S. Application Data

(63) Continuation-in-part of application No. 09/404,111, filed on Sep. 23, 1999, now Pat. No. 6,689,387.

(51) Int. Cl.
*A61K 31/40* (2006.01)
*A61K 9/16* (2006.01)
*A61K 9/127* (2006.01)

(52) U.S. Cl. ............... 514/419; 424/439; 424/1.13

(58) Field of Classification Search ............ None
See application file for complete search history.

(56) References Cited

U.S. PATENT DOCUMENTS

| | | | |
|---|---|---|---|
| 5,830,887 | A | 11/1998 | Kelly |
| 5,895,787 | A | 4/1999 | Arffmann et al. |
| 5,948,808 | A | 9/1999 | Safe |
| 5,981,568 | A * | 11/1999 | Kunz et al. ............ 514/411 |
| 6,001,868 | A * | 12/1999 | Firestone et al. ......... 514/415 |
| 6,086,915 | A | 7/2000 | Zeligs |
| 6,399,645 | B1 | 6/2002 | Bell et al. |
| 6,534,085 | B1 | 3/2003 | Zeligs |
| 6,613,792 | B1 | 9/2003 | Ellenberger et al. |
| 6,689,387 | B1 | 2/2004 | Zeligs |
| 2002/0147155 | A1 | 10/2002 | Foster et al. |
| 2003/0096855 | A1 | 5/2003 | Zeligs |
| 2004/0072891 | A1 | 4/2004 | Zeligs |
| 2004/0156910 | A1 | 8/2004 | Zeligs |

OTHER PUBLICATIONS

Liang Jin et al (Liang, j. et al. cancer research 1999, 59, 3991-3997).*
Baugh SM et al., "Treatment of cervical dysplasia with indole-3-carbinol" in The Ray A. Barlow Scientific Symposium, Jan. 23, 1998, Shreveport : The Center for Excellence in Cancer Research, Treatment and Education, Louisiana State University Medical Center, Shreveport (LA), p. 3.
Bell, MC et al., "Placebo-controlled Trial of Indole-3-Carbinol in the Treatment of Cervical Dysplasia", Mar. 1999, Gynecol. Oncol. 72:446.
Yuan F et al., "Prevention of Papillomavirus initiated cancer by the phytochemical Indole-3-Carbinol", Proceedings of the 17th International Papillomavirus Conference, Jan. 9-15, 1999, p. 73.

BioResponse-DIM Indolplex Product Information Brochure, Dec. 15, 1998.
Dec. 1998 Bioresponse Letter, Dec. 29, 1998.
Zeligs MA, "Diet and Estrogen Status: The Cruciferous Connection", 1998, J Med Food, 1:67-82.
Ponten J and Guo Z, "Precancer of the Human Cervix ", 1998, Cancer Surveys 32:201-229.
Cancer Medicine 3rd edition, 1993, JF Holland ed., Lea & Febiger, Malvern, PA p. 1633.
Molecular Biology of the Cell $2^{nd}$ ed., 1989, Alberts, B et al., Garland Publishing, Inc., New York, pp. 1193-1194, 1204-1206.
Arbeit, JM et al., "Chronic estrogen-induced cervical and vaginal squamous carcinogenesis in human papillomavirus type 16 transgenic mice", Apr. 1996, Proc Natl Acad Sci, USA 93:2930-2935.
Bell, MC et al., "Placebo-Controlled Trial of Indole-3-Carbinol in the Treatment of CIN", 2000, Gynecologic Oncology, 78:123-129.
Bradfield et al., "High-performance liquid chromatographic anaylsis of anticarcinogenic indoles in *Bassica oleracea*", 1987, J Agric Food Chem 35:46-49.
Michnovicz et al., "Changes in levels of urinary extrogen metabolites after oral indole-3-carbinol treatment in humans", 1997, J Natl Cancer Inst 89:718-23.
Ho et al., "Urinary $2/_{16}$ alpha-hydroestrone ratio: correlation with serum insulin-like growth factor binding protein-3 and and potential biomarker of breast cancer risk", 1998, Ann Acad Med Singapore 27:294-9.
Schneider et al., "Abnormal oxidative metabolism of estradiol in women with breast cancer", 1982, Proc Natl Acad Sci USA 79:3047-52.
Bradlow et al., "2-hydroxyestrone: the 'good' estrogen", J Endocrin 150:S259-S265.
Komura et al., "Catecholestrogen as a natural antioxidant", 1996, Ann NY Acad Sci 786:419-29.
Rosen et al., "Preliminary results of the use of indole-3-carbinol for recurrent respiratory papillomatosis", 1998, Otolaryngol Head Neck Surg 118:810-5.
Jin et al., "Indole-3-carbinol prevents cervical cancer in human papillomavirus type 16 (HPV16) transgenic mice", 1999, Cancer Res 59"3991-7.
Chen et al., "aryl hydrocarbon receptor-mediated antiestrogenic and antitumorigenic activity of diindoylmethane", 1998, Carcinogenesis 19:1631-1639.
Auborn et al., 2000, "Treatment of Human Papillomavirus Gynecologic Infections", Clin Lab Med 20:407-22.
Bradlow et al. "Multifunctional aspects of the action of indole-3-carbinol as an anyi-tumor agent," Annals of New York Academy of Sciences, 1999, vol. 889, pp. 204-213.

(Continued)

Primary Examiner—Michael G. Hartley
Assistant Examiner—Nabila Ebrahim

(57) ABSTRACT

New compositions are disclosed that comprise the phytochemical Diindolylmethane (DIM), as well as its precursor, Indole-3-carbinol (I3C), and cogener, 2-(Indol-3-ylm-ethyl)-3,3'diindolylmethane (LTr-1), acceptable carriers and/or excipients. These compositions are administered to prevent or reduce symptoms associated with mastalgia, endometriosis and HPV-related conditions including cervical dysplasia.

16 Claims, No Drawings

OTHER PUBLICATIONS

Chang et al., 1999, "Cytostatic and antiestrogenic effects of 2-(Indol-3-ylmethyl)-3,3'-diindolylmethane, a major in vivo product of dietary indole-3-carbinol," Biochem. Pharmacol. 58:825-834.

Dashwood, R.H., 1998, "Indole-3-carbinol: anticarcinogen or tumor promoter in brassica vegetables?" Chem Biol. Interact., 110(1-2):1-5.

de Vet et al., 1994, "The role of cigarette smoking in the etiology of cervical dysplasia," Epidemiology 5:631-633.

Exon, et al., 2000, "Dietary indole-3-carbinol alters immune functions in rats," J. Toxicol. Environ. Health A., 59(4):271-9.

Gillner et al., 1985, "Interactions of indoles with specific binding sites for 2,3,7,8-tetrachlorodibenzo-p-dioxin in rat lier," Mol Pharmacol 28:357-363.

Gooptu et al., 2000, "Treatment of viral warts with cimetidine: and open-label study," Clin. Exp. Dermatol. 25(3):183-5.

Hardman, et al. "Goodman & Gilman's The Pharmacological Basis of Therapeutics" (9th ed, 1996) pp. 51 and 57-58.

Larson-Su et al., 2001, "Transplacental exposure to indole-3-carbinol induces sex-specific expression of CYP1A1 and CYP1B1 in the liver of Fischer 344 neonatal rats," Toxicological Sci. 64:162-168.

Liu et al., 1994, "Indolo[3,2-b]carbozole: a dietary-derived factor the exhibits both antiestrogenic and estrogenic activity," J. Natl. Cancer Inst. 86:1758-1765.

Loub et al., 1975, "Aryl hydrocarbon hydroxylase induction in rat tissues by naturally occurring indoles of cruciferous plants," J. Natl. Cancer Inst. 54:985-988.

Michnovicz et al., 1991, "Cimetidine inhibits catechol estrogen metabolism in women," Metabolism, 40(2):170-74.

Michnovicz et al., 1986, "Increased 2-hydroxylation of estradiol as a possible mechanism for the anti-estorgenic effect of cigarette smoking," N Engl J Med 315:1305-1309.

Michnovicz et al., 1988, "Increased urinary catechol estrogen excretion in female smokers," Steroids 52:69-83.

Riby et al., 2000, "Ligand-independent activation of estrogen receptor function by 3,3'-diindolylmethane in human breast cancer cells," Biochem. Pharmacol. 60:167-177.

Ritter et al., 2001, "Oxidations of 17beta-estradiol and estrone and their interconversions catalyzed by liver, mammary gland and mammary tumor after acute and chronic treatment of rats with indole-3-carbinol or beta-naphthoflavine," Can. J. Physiol. Pharmacol. 79(6):519-32.

Schwartz et al., Journal of Cellular Biochemistry, (1995) 58/Suppl. 22,(210-217).

Sepkovic et al., 2002, "Quantitative Determination of 3,3'-Diindolymethane in the urine of individuals receiving indole-3-carbinol," Nutr Cancer. 2001;41(1-2):57-63.

Shilling et al., 2001, "3,3'-diindolylmethane, a major condensation product of indole-3-carbinol, is a potent estrogen in the rainbow trout," Toxicology and Applied Pharmacology 170:191-200.

Stresser et al., 1995, "Mechanisms of tumor modulation by indole-3-carbinol: disposition and excretion in male fisher 344 rats," Drug Metabolism and Disposition 23:965-975.

Stresser et al., 1995, "The anticarcinogen 3,3'-Diindolyl-methane is an inhibitor of cytochrome P-450," J. Biochem. Toxicol., 10(4):191-201.

Tse et al., 1987, "Disposition of alpha-[(dimethylamino)methyl]-2-(3-ethyl-5-methyl-4-isoxazolyl)-1H-indole-3-methanol (59-801), a hypoglycaemic agent in rats, dogs and monkeys," Xenobiotica, 17(6):741-9.

Walboomers et al., 1999, "Human papillomavirus is a necessary cause of invasive cervical cancer worldwide," J. Pathol. 189:12-19.

\* cited by examiner

PHYTOCHEMICALS FOR THE TREATMENT OF CERVICAL DYSPLASIA

CROSS REFERENCE TO RELATED APPLICATIONS

This application is a continuation-in-part of prior application Ser. No. 09/404,111, filed Sep. 23, 1999, now U.S. Pat. No. 6,689,387 the entire contents of which are hereby expressly incorporated by reference.

1. FIELD OF THE INVENTION

The present invention relates to compositions and methods for prevention or reduction of symptoms associated with mastalgia, endometriosis and Human Papilloma Virus-related conditions including, but not limited to, cervical dysplasia, by administering indole phytochemicals. Among the indole phytochemicals useful in the compositions and methods of the invention are diindolylmethane (DIM), and its cogener, 2-(Indol-3-ylmethyl)-3,3'-diindolylmethane (LTr-1).

2. BACKGROUND OF THE INVENTION

2.1. Introduction

In the typical life-cycle of modern women, the mid-thirties until the cessation of menstrual periods is defined as "peri-menopause". Women are classified as perimenopausal if menses have been experienced in the last 12 months, but with irregularity or changes in menstrual flow. During this stage of life women suffer increasing incidence of both recurrent breast pain, or "mastalgia", and endometriosis, describing the painful condition of persistence of abnormal endometrial tissue in the abdominal cavity. These two conditions, common to the perimenopause, are poorly understood and presently lack medical therapy that is both effective and reasonably free of side effects (Prior J C, 1998, "Perimenopause: the complex endocrinology of the menopausal transition", Endocr. Rev. 19:397-428).

While a contributing role of estrogen status has been suspected in these conditions, few consistent abnormalities in endocrine status have been identified. Circulating estrogen levels are normal in both mastalgia and endometriosis patients. There is accumulating evidence that describes diminished progesterone production during the perimenopause that may create a relative "dominance" in the activity of estrogen. However, no one theory or endocrine imbalance explains the occurrence of mastalgia and endometriosis (Santoro N et al., 1996, "Characteristics of reproductive hormonal dynamics in the perimenopause", J. Clinical Endocrinology and Metab. 81:1495-501). Similarly, changes in estrogen to progesterone balance in women have not been associated with the occurrence of Human Papilloma Virus (HPV)-related cervical dysplasia.

2.2. Mastalgia

Recurrent, cyclical breast pain or "mastalgia" is one of the most common reasons for women's visits to their doctors. It has been estimated that 50-70% of all women experience significant mastalgia at some point in their life. In its most common form, mastalgia is a chronic condition of recurring pain, which is worse during the few days before menses (Blue J et al., 1998, "Mastalgia review: St. Marks Breast Centre", New Zealand Medical Journal 111(1059):33-34). Traditionally, treatment choices for mastalgia have ranged from dietary manipulation (caffeine, fat, and alcohol reduction) or evening primrose oil to hormonal medications (bromocriptine and danazol) for severe breast pain. Bromocriptine (Parlodel) and danazol have a response rate of 70%, but have reported adverse side effects of up to 30-35% (Gateley C A and Mansen R E, 1991, "Management of the painful and nodular breast", British Medical Bulletin 47:284-94; Nazli K et al., 1989, "Controlled trial of the prolactin inhibitor bromocriptine (Parlodel) in the treatment of severe cyclical mastalgia", British Journal of Clinical Practice 43(9):322-7; Kontosolis K et al., 1997, "Comparison of tamoxifen with danazol for treatment of cyclical mastalgia", Gynecol. Endocrinol. 11:393-397). The use of medroxyprogesterone acetate to support levels of progesterone, possibly low in this condition, provided relief no better than placebo in a controlled trial (Maddox P R et al., 1990, "A randomized controlled trial of medroxyprogesterone acetate in mastalgia", Annals of the Royal College of Surgeons of England 72(2):71-6).

The approach of dietary supplementation for mastalgia has been explored by earlier investigators. This included the addition of high doses of evening primrose oil, beta carotene, and vitamin A to the diet of affected women. Evening primrose oil is used by British physicians as an initial intervention to control mastalgia because of its non-hormonal composition. Though it has been found to normalize the ratio of essential fatty acids to saturated fatty acids in the serum of women with mastalgia, the therapy requires 3 to 4 months for benefit. Improvements were seen in up to 40% of patients but side effects included bloating and nausea (Maddox P R, 1989, "The management of mastalgia in the UK", Hormone Research 32:21-27). Italian researchers explored the addition of combinations of beta carotene and Vitamin A (retinol) in the management of mastalgia. (Santamaria L et al., 1989, "Beta-carotene supplementation associated with intermittent retinol administration in the treatment of premenopausal mastodynia", Boll Chim Far 128:284-287). Some success was reported, but the high doses of retinol required (150-300,000 I.U per day) are in the range associated with significant side effects which include headache, skin lip and mouth dryness, nausea, dizziness, and alopecia. Based on the common occurrence of mastalgia as a disorder in women, the need exists for more effective therapy with acceptable risks and side effects (Ashley B, 1998, "Mastalgia", Lippincotts Primary Care Practice 2(2):189-93).

2.3. Endometriosis

Endometriosis is a disease that affects as many as 15% of fertile women and up to 50% of infertile women. Its occurrence increases with age and is greatest in the perimenopausal years (Tzingounis V A and Cardamakis E, 1997, "Modem approach to endometriosis", Annals of the New York Academy of Sciences 816:320-330). Endometriosis refers to the presence of functional endometrial glands and stroma in abnormal locations outside the uterine cavity. Despite extensive research, the natural history and pathogenesis of endometriosis is still poorly understood and remains controversial. As with mastalgia, most therapeutic approaches have been directed at hormonal therapy. The most common therapy involves the use of Danazol. Danazol is a synthetic steroid with androgenic action suppressing the pituitary gland cycling necessary for menstrual periods. Amenorrhea, or lack of menstrual periods results. Though providing some relief from the pain of endometriosis adverse side effects are experienced in up to 80% of women using Danazol (Greenblatt R B et al., 1971, "Clinical studies with an anti-gonadotropin—danazol", Fertil Steril 22:102). Notably these side effects include weight gain, fluid retention, acne, decreased breast size, hot flushes and mood changes. In addition to Danazol, other hormonal manipulations used in the management of endometriosis involve use of gonadotropin releasing hormone analogues (GnRH) and the drug gestrinone, a synthetic steroid derived from 19-nortestosterone. The side effects associated with these therapies are significant and include the spectrum of symptoms associated with hypoestrogenism and menopause.

These include hot flushes, night sweats, and osteoporosis (Telimaa E J et al., 1987, "Placebo-controlled comparison of danazol and high-dose medroxyprogesterone acetate in the treatment of endometriosis", Gynecol Endocrinol 1:51; Thomas E. J. et al., 1987, "Impact of gestrinone on the course of asymptomatic endometriosis", Br. Med J., 294:272). Clearly, more benign approaches to the management of the pain of endometriosis are needed.

2.4. Cervical Dysplasia

Cervical dysplasia, also known as cervical intraepithelial neoplasia (CIN), refers to the occurrence of abnormal cells and tissue involving the surface of the uterine cervix, which consists of the lowest part of the uterus. Anatomically, the cervix provides the portal of entry from the vagina to the interior of the uterus. Its surface consists of an epithelial "transition-zone" where superficial, flattened cells characteristic of vaginal mucosa abruptly change to cuboidal epithelial cells characteristic of the interior surface of the uterus (endometrium). The designations CIN I, II and III refer to mild, moderate, and severe dysplasia/carcinoma in situ (CIS) of the cervical epithelium, respectively. This histological grading scheme is based largely on the extent to which the thickness of the epithelium is replaced by abnormal, mitotically active cells with enlarged, hyperchromatic nuclei (Ferenczy A et al., "Cervical Intraepithelial Neoplasia and Condyloma", In R. J. Kurman, Editor. Blaustein's Pathology of the Female Genital Tract, Springer-Verlag, 1987). Untreated, a subset of dysplastic lesions will advance to cervical cancer, with a frequency that increases dramatically in CIN III lesions (Ostor A G, 1993, Int. J. Gynecol. Path. 12:186-192).

In many developing countries, cervical cancer is the most common cancer (excluding skin) in women and the major cause of cancer-related deaths in women (Parkin D et al., 1993, Int J Cancer 54:594-606). In the United States, abnormalities on Papanicolaou, or "Pap" smears are detected in millions of women annually, resulting in an estimated annual cost of $6 billion for patient evaluation and treatment (Kurman R et al., 1994, JAMA 271:1866-9).

Cervical dysplasia in women is a common condition that is linked to infection by HPV (Walboomers J M et al., 1999, "Human papillomavirus is a necessary cause of invasive cervical cancer worldwide", J Pathol. 189(1):12-9). While dependent on the presence of HPV, the occurrence of cervical dysplasia in women has not been related to estrogen or progesterone levels. Regarding estrogen metabolism, the severity of cervical dyplasia, documented by stage of CIN on biopsy, has been associated with a reduced 2-hydroxy metabolism of estrogen in some women (Sepkovic et al., 1995, "Estrogen Metabolite Ratios and Risk Assessment of Hormone-related Cancers", Annals New York Academy of Sciences 768:312-316).

The most common methods used to treat cervical dysplasia include removal or eradication of the abnormal tissue, using methods such as cryosurgery, laser vaporization, and surgical removal. Due to the potential for harm to normal tissue, and recurrence of dysplasia following surgery, a need clearly exists for more effective and less invasive therapy.

2.5. Dietary Indoles 3,3'-Diindolylmethane (DIM), as well as its precursor, Indole-3-carbinol (I3C), and cogener, 2-(Indol-3-ylmethyl)-3,3'-diindolylmethane (LTr-1), are natural phytochemicals and part of the family of dietary indoles discovered in cruciferous vegetables. DIM and I3C are found in cruciferous vegetables including broccoli, cauliflower, cabbage and Brussels sprouts (Bradfield C A and Bjeldanes L F, 1987, "High performance liquid chromatographic analysis of anticarcinogenic indoles in Brassica oleracea", J. Agric. Food Chem. 35:46-49). DIM, together with the linear trimer, LTr-1, are formed after the enzymatic release of I3C from parent glucosinolates found in all cruciferous vegetables.

It is now known that there is a connection between dietary cruciferous indoles and estrogen metabolism. H. Leon Bradlow, Ph.D. and his group at the Strang Cancer Prevention Laboratory in New York were the first to establish the link between phytonutrients from cruciferous vegetables and estrogen metabolism. They showed that supplemental use of I3C can act to promote a dramatic change in the metabolism of estrogen (Michnovicz J J et al., 1997, "Changes in levels of urinary estrogen metabolites after oral indole-3-carbinol treatment in humans", J Natl Cancer Inst. 89(10):718-23). This change in metabolism has the power to greatly reduce estrogen exposure as a risk for cancer and provides a dietary approach to improving estrogen metabolism. I3C has been shown to increase 2-hydroxy estrogen metabolism in women (Bradlow H L et al., 1994, "Long-term responses of women to indole-3-carbinol or a high fiber diet", Cancer Epidemiol Biomarkers Prev. 3(7):591-5). When cruciferous phytochemicals are added to the diet, estrogen metabolism is shifted. This produces a predominance of 2-hydroxy and 2-methoxyestrogens (Michnovicz J J et al., 1997, "Changes in levels of urinary estrogen metabolites after oral indole-3-carbinol treatment in humans", J Natl Cancer Inst. 89(10): 718-23). An increased proportion of 2-hydroxy metabolites is correlated to protection from breast cancer. This relationship has been documented in case-control studies (Ho G H et al., 1998, "Urinary 2/16 alpha-hydroxyestrone ratio: correlation with serum insulin-like growth factor binding protein-3 and a potential biomarker of breast cancer risk", Ann Acad Med Singapore 27:294-299; Schneider J. et al., 1982, "Abnormal oxidative metabolism of estradiol in women with breast cancer", Proc Natl Acad Sci USA 79:3047-3051). The 2-hydroxy metabolites have been called "good estrogens" (Bradlow H L et al., 1996, "2-hydroxyestrone: the 'good' estrogen", J Endocrinol. 150 Suppl:S259-65), and may function as antioxidants (Komura S et al., 1996, "Catecholestrogen as a natural antioxidant", Ann N Y Acad Sci. 786:419-429).

With regard to prior art and the dietary indoles, the supplemental use of I3C, which converts in part to DIM, LTr-1, and other compounds after passage through the stomach, has been the subject of U.S. Pat. No. 5,895,787, describing the use of I3C and related dietary indoles to reduce the symptoms of fibromyalgia. Despite this use, no relationship between fibromyalgia and estrogen status has been documented (Bengtsson A. and Henriksson, K. G., 1986, "Primary fibromyalgia. A clinical and laboratory study of 55 patients", Scand J. Rheumatol 15(3):340-7). Published reports have demonstrated some clinical improvement following dietary supplementation with I3C in recurrent laryngeal papillomatosis and cervical dysplasia (Rosen C A et al., 1998, "Preliminary results of the use of indole-3-carbinol for recurrent respiratory papillomatosis", Otolaryngology Head Neck Surgery 118: 810-5; Jin L. et al., 1999, "Indole-3-carbinol prevents cervical cancer in human papilloma virus type 16 (HPV16) transgenic mice", Cancer Res. 59(16): 3991-7; Baugh S M et al., 1998, "Treatment of cervical dysplasia with indole-3-carbinol", Ray A. Barlow Scientific Symposium, Louisiana State University Medical School, Shreveport, La.; Bell M C et al., 2000, "Placebo-controlled trial of indole-3-carbinol in the treatment of CIN", Gynecol Oncol. 78(2):123-9). These diseases are both conditions related to the presence of the human papilloma virus. Reports of adverse side effects with I3C use in animals and in at higher doses in individuals with respiratory HPV infection (Recurrent Respiratory Papillomatosis ["RRP"]) have discouraged further clinical testing of I3C (Rosen C A et al., 1998, "Preliminary results of the use of indole-3-carbinol for recurrent respiratory papillomatosis", Otolaryngology Head Neck Surgery 118:810-5; Wilker C et al., 1996, "Effects of developmental exposure to indole-3-carbinol or 2,3,7,8-tetrachlorodibenzo-p-dioxin on reproductive potential of male rat offspring", Toxicol Appl Pharmacol. 141(1): 68-75). I3C's use is associated with a number of safety concerns in reproductive-age women due to its enzyme-inducing actions and developmental toxicity.

Thus, the individual metabolic products of I3C are being investigated to discover safer and more effective alternatives to I3C. Following oral administration of I3C, DIM is but one of many derivatives generated from I3C. I3C is highly reactive in stomach acid, which leads to the production of a large number of biologically active byproducts distinct from DIM. DIM arises from I3C as one of the reaction products in more neutral pH environments, not typically seen in the gastric environment. I3C exposure to acid produces many non-DIM products, including indolo(3,2,b)carbazole (ICZ), and the cyclic trimer, 5,6,11,12,17,18-hex-hydrocyclononal [1,2-b:4,5-b':7,8-b]:triindole, and others which are more highly enzyme inductive than DIM (De Kruif C A et al., 1991, "Structure elucidation of acid reaction products of indole-3-carbinol: detection in vivo and enzyme induction in vitro", Chem Biol Interact 80(3):303-15).

DIM differs from I3C in its structure and in its chemical and biological properties. Unlike I3C, DIM is an acid-stable indole with less influence on carcinogen metabolism than I3C and non-DIM products from I3C (Bradfield C A and Bjeldanes L F, 1987, "Structure-activity relationships of dietary indoles: a proposed mechanism of action as modifiers of xenobiotic metabolism", J Toxicol Environ Health 21(3):311-23). Unlike I3C, DIM has been shown to influence estrogen metabolism in animals without the need for intra-gastric conversion into other indole reaction products (Jellinck P H et al., 1993, "Ah receptor binding properties of indole carbinols and induction of hepatic estradiol hydroxylation", Biochem Pharmacol 45:1129-1136).

In cell culture, DIM has been shown to have both growth promoting and growth inhibitory properties. In MCF7 breast cancer cells, DIM promoted growth when tested in the absence of estrogen (Riby J E et al., 2000, "Ligand-independent activation of estrogen receptor function by 3,3'-diindolylmethane in human breast cancer cells", Biochem Pharmacol 60(2):167-77). When tested in colon cancer cells, DIM demonstrated selective growth inhibitory activity which was not observed in non-cancerous colon cells (Gamet-Payrastre L et al., 1998, "Selective cytostatic and cytotoxic effects of glucosinolates hydrolysis products on human colon cancer cells in vitro", Anti-Cancer Drugs 9:141-148).

In another study, oral DIM was shown to impede the growth of carcinogen-induced breast cancer in animals (Chen I. et al., 1998, "Aryl hydrocarbon receptor-mediated antiestrogenic and antitumorigenic activity of diindolylmethane", Carcinogenesis 19(9):1631-9).

There have been no reports on the usefulness of DIM or LTr-1 in the treatment or prevention of mastalgia, endometriosis or HPV-related conditions, including cervical dysplasia. Isolation and formulation requirements for DIM as a pure substance limited its availability for animal experiments. Pure, isolated DIM was not available for human use prior to Summer, 1998. Use of DIM and LTr-1 in absorption enhancing formulations for improving the balance of estrogen metabolites has been the subject of earlier investigation by the present inventor and provides the basis of U.S. Pat. No. 6,086,915. This work has allowed for the present investigation of the use of dietary indoles as dietary supplements to beneficially impact mastalgia, endometriosis, and cervical dysplasia.

Therefore, safer and more consistently effective treatments are needed for mastalgia, endometriosis and HPV-related conditions, including cervical dysplasia.

3. SUMMARY OF THE INVENTION

The present invention relates to compositions and methods for prevention or reduction of symptoms associated with mastalgia, endometriosis and HPV-related diseases including, but not limited to, cervical dysplasia, by administering phytochemicals, e.g., dietary indoles. In a preferred embodiment, the pain associated with endometriosis and mastalgia is prevented or reduced. In another embodiment, the presence of a marker associated with endometriosis is reduced through phytochemical treatment. In yet another preferred embodiment, the progression of cervical dysplasia to cervical cancer is prevented or cervical dysplasia is reduced and/or eliminated. Among the phytochemicals useful in the compositions and methods of the invention are diindolylmethane (DIM), and its cogener, 2-(Indol-3-ylmethyl)-3,3'-diindolylmethane (LTr-1).

Also according to the present invention, a pharmaceutical composition is provided, which comprises a phytochemical, preferably DIM and/or LTr-1, and, optionally, pharmaceutically acceptable carriers.

In one aspect, the present invention provides a method of treating cervical dysplasia in a subject having cervical dysplasia comprising administering to the subject an amount of a dietary indole selected from the group consisting of DIM and LTr-1 effective to reduce one or more symptoms associated with cervical dysplasia. In a preferred embodiment, the dietary indole is DIM. In a more preferred embodiment, DIM is suspended as microparticles in a starch carrier matrix. In other embodiments, the dietary indole is formulated as a cream or suppository. In certain embodiments, the dietary indole is administered by direct application to the vaginal or cervical mucosa of the subject. In certain embodiments, the dietary indole is formulated as a cream, and is administered transdermally. In certain embodiments, the dietary indole is administered orally.

In another aspect, the present invention provides a method of preventing cervical dysplasia in a subject in danger of developing cervical dysplasia comprising administering to the subject an amount of a dietary indole selected from the group consisting of DIM and LTr-1 effective to prevent one or more symptoms associated with cervical dysplasia. In a preferred embodiment, the dietary indole is DIM. In a more preferred embodiment, DIM is suspended as microparticles in a starch carrier matrix. In other embodiments, the dietary indole is formulated as a cream or suppository. In certain embodiments, the dietary indole is administered by direct application to the vaginal or cervical mucosa of the subject. In certain embodiments, the dietary indole is formulated as a cream, and is administered transdermally. In certain embodiments, the dietary indole is administered orally.

4. DETAILED DESCRIPTION OF THE INVENTION

The present invention is based upon the observation that administration of phytochemicals, in particular, DIM, and LTr-1, has improved symptoms of mastalgia, endometriosis, and HPV-related conditions, including cervical dysplasia. In particular, the administration of DIM, either topically and orally, is followed by a therapeutic response in mastalgia and cervical dysplasia.

The facilitated delivery of DIM and related indoles as dietary supplements may be accomplished according to formulations and methods described in U.S. Pat. No. 6,086, 915. The effectiveness of supplemental DIM is further supported by co-administration of phytochemicals (e.g., DIM, LTr-1) with grapefruit concentrate, which additionally facilitates the absorption of phytochemicals (e.g., DIM, LTr-1).

4.1. Methods of Treating Mastalgia

The invention provides compositions and methods for prevention or reduction of symptoms associated with mastalgia. In a preferred embodiment, breast pain of subjects suffering from mastalgia is prevented, reduced and/or eliminated through the administration of phytochemicals, e.g., dietary indoles, in a pharmaceutically acceptable fashion. In preferred embodiments, the phytochemicals are DIM, I3C and LTr-1. In particular embodiments, I3C, DIM, or LTr-1, alone or in combination with each other or other dietary supplements, are administered orally in, for example, the form of encapsulated dietary supplements.

The I3C is preferably administered at a dose of 200-500 mg per day. In alternative embodiments, I3C is administered at doses of 200-300 mg per day, 300-400 mg per day and 400-500 mg per day.

DIM is administered providing 150-500 mg per day of DIM. In preferred embodiments, the dose of DIM, I3C or LTr-1 is 150-200 mg per day, 200-300 mg per day, 300-400 mg per day, and 400-500 mg per day.

In a preferred embodiment, DIM is administered in an absorption enhancing formulation, as described in U.S. Pat. No. 6,086,915, providing 60-500 mg per day of DIM suspended as microparticles in a starch carrier matrix. In preferred embodiments, the dose of processed DIM is 60-100 mg per day, 100-200 mg per day, 200-300 mg per day, 300-400 mg per day, and 400-500 mg per day.

The LTr-1 is preferably administered in an absorption enhancing formulation providing 60-500 mg per day of LTr-1 suspended as microparticles in a starch carrier matrix as previously described, however, the present invention contemplates the administration of any preparation of LTr-1. In a preferred embodiment, the dose of LTr-1 is 150-200 mg per day. In preferred embodiments, the dose of processed LTr-1 is 60-100 mg per day, 200-300 mg per day, 300-400 mg per day, and 400-500 mg per day.

Doses of the phytochemicals of the invention can also be calculated based upon the body weight of the subject to be treated. Doses of phytochemicals between 0.5 and 3 mg per kg of body weight per day are preferred. In another preferred embodiment, the phytochemicals are administered at a dose of between 0.5 and 2.0 mg per kg per day, preferably 1.5 mg per kg per day.

Alternatively, the co-administration of grapefruit, grapefruit concentrate, grapefruit juice, or grapefruit juice concentrate, or other grapefruit-derived composition along with a dietary indole (e.g., I3C, DIM or LTr-1) can be used to increase absorption of the phytochemicals and promote even more efficient relief from the symptoms of mastalgia.

In an alternative embodiment, the dietary indole (e.g., DIM or LTr-1) is administered in the form of a liposomal sublingual spray applied directly to the oral mucosa. This liposomal suspension provides phytochemical loaded liposomes to administer the phytochemicals and create a sustained delivery system. Dietary indole (e.g., DIM or LTr-1) containing liposomes are sequestered in the oral mucosa, allowing absorption which avoids "first pass" hepatic metabolism. The liposomal spray uses standard liposomal preparation and structural lipid ingredients (Ranade V V, 1989, "Drug delivery systems. 1. Site-specific drug delivery using liposomes as carriers", J. Clin. Pharmacol. 29(8):685-94). In a preferred embodiment, the liposomal spray is administered at a dose of 5-30 mg of dietary indole (e.g., DIM or LTr-1) daily delivered in 2-12 sprays of a typical liposomal preparation.

Alternatively the phytochemicals (e.g., DIM or LTr-1) may be administered in the form of a transdermal cream applied directly to the skin. This cream utilizes various absorption enhancing emollients and consists of phytochemical (e.g., DIM or LTr-1) in a concentration of 1-3% by weight. It is designed as a moisturizing cosmetic that is formulated to allow application directly to painful breasts in women not wishing to take phytochemicals orally. Formulations are also made with the neurohormone, melatonin, to provide a nighttime cosmetic mosturizer offering the benefits of melatonin in combination with the phytochemical (e.g., DIM or LTr-1). This allows application of cruciferous indoles and melatonin directly to underlying breast tissue with the added benefit of sleep regulating action from melatonin. In a particular embodiment, application of from 5-10 cc of the transdermal preparation daily is used to administer from 5-30 mg of DIM or other dietary indole per day, and optionally, 3-10 mg of melatonin per day.

Alternatively, the phytochemical (e.g., DIM or LTr-1) may be administered in the form of a vaginal cream or suppository containing microcrystalline phytochemical (e.g., DIM or LTr-1) in a combined dose of 20-100 mg. This allows application of cruciferous indoles directly to vaginal and cervical mucosa for the benefit of cervical dysplasia.

The phytochemicals of the invention may be administered in any appropriate amount in any suitable galenic formulation and following any regime of administration.

The actual administered amount of phytochemical may be decided by a supervising physician and may depend on multiple factors, such as, the age, condition, file history, etc., of the patient in question.

The subject, or patient, to be treated using the methods of the invention is an animal, e.g., a mammal, and is preferably human, and can be a fetus, child, or adult. In a preferred embodiment, the subject is a human female.

4.2. Methods of Treating Endometriosis

The invention provides compositions and methods for reduction or prevention of symptoms associated with endometriosis. In a preferred embodiment, the pain of subjects suffering from endometriosis is prevented, reduced and/or eliminated through the administration of phytochemicals in a pharmaceutically acceptable fashion. In another preferred embodiment, the levels of an endometriosis marker (e.g., Ca-125 antigen, a serum marker of endometriosis) in subjects suffering from endometriosis is lowered through the administration of phytochemicals in a pharmaceutically acceptable fashion. In preferred embodiments, the phytochemicals are DIM, I3C and LTr-1. In particular embodiments, DIM, or LTr-1, alone or in combination with each other or other dietary supplements, are administered orally in, for example, the form of encapsulated dietary supplements.

DIM is administered providing 30-500 mg per day of DIM. In preferred embodiments, the dose of DIM, I3C or LTr-1 is 30-100 mg per day, 100-200 mg per day, 200-300 mg per day, 300-400 mg per day, and 400-500 mg per day.

In a preferred embodiment, DIM is administered in an absorption enhancing formulation, as described in U.S. Pat. No. 6,086,915, providing 30-500 mg per day of DIM suspended as microparticles in a starch carrier matrix. In preferred embodiments, the dose of processed DIM is 30-100 mg per day, 100-200 mg per day, 200-300 mg per day, 300-400 mg per day, and 400-500 mg per day.

The LTr-1 is preferably administered in an absorption enhancing formulation providing 30-400 mg per day of LTr-1 suspended as microparticles in a starch carrier matrix as previously described, however, the present invention contemplates the administration of any preparation of LTr-1. In a preferred embodiment, the dose of LTr-1 is 100-200 mg per day. In preferred embodiments, the dose of processed LTr-1 is 30-100 mg per day, 200-300 mg per day, 300-400 mg per day, and 400-500 mg per day.

Doses of the phytochemicals of the invention can also be calculated based upon the body weight of the subject to be treated. Doses of phytochemicals between 1 and 3 mg per kg of body weight per day are preferred. In another preferred embodiment, the phytochemicals are administered at a dose of between 1.5 and 2.5 mg per kg per day, preferably 2.0 mg per kg per day.

Alternatively, the co-administration of grapefruit, grapefruit concentrate, grapefruit juice, or grapefruit juice concentrate, or other grapefruit-derived composition along with I3C, DIM or LTr-1 can be used to increase absorption of the phytochemicals and promote even more efficient relief from the symptoms of endometriosis, including the reduction of markers associated with endometriosis.

In an alternative embodiment, the phytochemical (e.g., DIM or LTr-1) is administered in the form of a liposomal sublingual spray applied directly to the oral mucosa. This liposomal suspension provides phytochemical loaded liposomes to administer the phytochemicals and create a sustained delivery system. DIM and LTr-1 containing liposomes are sequestered in the oral mucosa, allowing absorption which avoids "first pass" hepatic metabolism. The liposomal spray uses standard liposomal preparation and structural lipid ingredients (Ranade V V, 1989, "Drug delivery systems. 1. Site-specific drug delivery using liposomes as carriers," J. Clin. Pharmacol. 29(8):685-94; Crommelin D J A and Schreir H, "Liposomes", Colloidal Drug Delivery Systems, Kreuter, J. editor, Marcel Dekker, N.Y., 1994, p. 85). In a preferred embodiment, the liposomal spray is administered at a dose of 5-30 mg of phytochemical daily delivered in 2-12 sprays of a typical liposomal preparation.

Alternatively the phytochemicals (e.g., DIM or LTr-1) may be administered in the form of a transdermal cream applied directly to the skin. This cream utilizes various absorption-enhancing emollients and consists of DIM or LTr-1 in a concentration of 1-3% by weight. It is designed as a moisturizing cosmetic which is formulated to allow application directly to the skin of women not wishing to take phytochemicals orally. Formulations are also made with the neurohormone, melatonin, to provide a nighttime cosmetic moisturizer offering the benefits of melatonin in combination with the phytochemical (e.g., DIM or LTr-1). This provides the added benefit of sleep regulating action from melatonin. In a particular embodiment, application of from 5-10 cc of the transdermal preparation daily is used to administer from 5-30 mg of phytochemical (e.g., DIM or LTr-1) per day, and optionally, 3-10 mg of melatonin per day.

Alternatively the phytochemical (e.g., DIM or LTr-1) may be administered in the form of a vaginal cream or suppository containing microcrystalline DIM or LTr-1 in a combined dose of 20-100 mg. This allows application of cruciferous indoles directly to vaginal and cervical mucosa for the benefit of cervical dysplasia.

The phytochemicals of the invention may be administered in any appropriate amount in any suitable galenic formulation and following any regime of administration.

The actual administered amount of phytochemical may be decided by a supervising physician and may depend on multiple factors, such as, the age, condition, file history, etc., of the patient in question.

The subject, or patient, to be treated using the methods of the invention is an animal, e.g., a mammal, and is preferably human, and can be a fetus, child, or adult. In a preferred embodiment, the subject is a human female.

4.3. Methods of Treating HPV-Related Conditions, Including Cervical Dysplasia

The invention provides compositions and methods for prevention or reduction of symptoms associated with cervical dysplasia, a known HPV-related condition. In a preferred embodiment, the progression of cervical dysplasia to cervical cancer is prevented or cervical dysplasia is reduced and/or eliminated through the administration of phytochemicals in a pharmaceutically acceptable fashion. In preferred embodiments, the phytochemicals are DIM and LTr-1. In particular embodiments, DIM, or LTr-1, alone or in combination with each other or other dietary supplements, are administered orally in, for example, the form of encapsulated dietary supplements.

DIM is administered providing 30-500 mg per day of DIM. In a preferred embodiment, DIM is administered providing 150-500 mg per day of DIM. In more preferred embodiments, the dose of DIM or LTr-1 is 30-100 mg per day, 100-200 mg per day, 150-200 mg per day, 200-300 mg per day, 300-400 mg per day, and 400-500 mg per day.

In a preferred embodiment, DIM is administered in an absorption enhancing formulation, as described in U.S. Pat. No. 6,086,915, providing 30-500 mg per day of DIM, preferably 60-500 mg per day, of DIM suspended as microparticles in a starch carrier matrix. In preferred embodiments, the dose of processed DIM (25% DIM by weight of the formula) is 30-100 mg per day, 60-100 mg per day, 100-200 mg per day, 200-300 mg per day, 300-400 mg per day, and 400-500 mg per day. In more preferred embodiments, the dose of processed DIM (25% DIM by weight of the formula) is 120-400 mg per day, 240-400 mg per day, 400-800 mg per day, 800-1,200 mg per day, 1,200-1600 mg per day, and 1,600-2,000 mg per day.

The LTr-1 is preferably administered in an absorption enhancing formulation providing 30-500 mg per day, preferably 60-500 mg per day, of LTr-1 suspended as microparticles in a starch carrier matrix as previously described, however, the present invention contemplates the administration of any preparation of LTr-1. In a preferred embodiment, the dose of LTr-1 is 100-200 mg per day, more preferably 150-200 mg per day. In preferred embodiments, the dose of processed LTr-1 is 30-100 mg per day, 60-100 mg per day, 200-300 mg per day, 300-400 mg per day, and 400-500 mg per day. In a preferred embodiment, the dose of LTr-1 is 100-200 mg per day, more preferably 150-200 mg per day. In preferred embodiments, the dose of processed LTr-1 is 120-400 mg per day, 240-400 mg per day, 800-1,200 mg per day, 1,200-1600 mg per day, and 1,600-2000 mg per day.

Doses of the phytochemicals of the invention can also be calculated based upon the body weight of the subject to be treated. Doses of phytochemicals between 0.5 and 5 mg per kg of body weight per day are preferred. Doses of phytochemicals between 1 and 3 mg per kg of body weight per day are preferred. In another preferred embodiment, the phytochemicals are administered at a dose of between 1.5 and 3.0 mg per kg per day, more preferably between 1.5 and 2.5 mg per kg per day, preferably 1.5 or 2.0 mg per kg per day.

Alternatively, the co-administration of grapefruit, grapefruit concentrate, grapefruit juice, or grapefruit juice concentrate, or other grapefruit-derived composition along with a dietary indole (e.g., DIM or LTr-1) can be used to increase absorption of the phytochemicals and promote even more efficient relief from the symptoms of cervical dysplasia.

In an alternative embodiment, the dietary indole (e.g., DIM or LTr-1) is administered in the form of a liposomal sublingual spray applied directly to the oral mucosa. This liposomal suspension provides phytochemical loaded liposomes to administer the phytochemicals and create a sustained delivery system. Dietary indole (e.g., DIM or LTr-1) containing liposomes are sequestered in the oral mucosa, allowing absorption which avoids "first pass" hepatic metabolism. The liposomal spray uses standard liposomal preparation and structural lipid ingredients (Ranade V V, 1989, "Drug delivery systems. 1. Site-specific drug delivery using liposomes as carriers," J. Clin. Pharmacol. 29(8):685-94). In a preferred embodiment, the liposomal spray is administered at a dose of 5-30 mg of dietary indole (e.g., DIM or LTr-1) daily delivered in 2-12 sprays of a typical liposomal preparation. In a preferred embodiment, the liposomal spray is administered at a dose of 15-130 mg of dietary indole (e.g., DIM or LTr-1) daily delivered in 2-12 sprays of a typical liposomal preparation.

Alternatively the phytochemicals (e.g., DIM or LTr-1) may be administered in the form of a transdermal cream or suppository applied directly to the skin, genitalia, or cervical epithelium. These topical formulations utilize various absorption enhancing emollients and consist of phytochemical (e.g., DIM or LTR) in a concentration of 1-3%, more preferably 1-2% by weight. This allows application of cruciferous indoles, DIM or LTR, directly to underlying cervical tissue. In a particular embodiment, application of from 5 to 10 cc of the transdermal preparation daily is used to administer from 5-30 mg of DIM per day to the skin. In a particular embodiment, application of from 5 to 10 cc of the transdermal preparation daily is used to administer from 50-100 mg of DIM per day to the skin.

Alternatively, the phytochemical (e.g., DIM or LTr-1) may be administered in the form of a vaginal cream or suppository containing microcrystalline phytochemical (e.g., DIM or LTr-1) in a combined dose of 20-100 mg per day, or 20-200 mg per day, more preferably 50-100 mg per day. This allows application of cruciferous indoles directly to vaginal and cervical mucosa for the benefit of cervical dysplasia.

The phytochemicals of the invention may be administered in any appropriate amount in any suitable galenic formulation and following any regime of administration.

The actual administered amount of phytochemical may be decided by a supervising physician and may depend on multiple factors, such as, the age, condition, file history, etc., of the patient in question.

The subject, or patient, to be treated using the methods of the invention is an animal, e.g., a mammal, and is preferably human, and can be a fetus, child, or adult. In a preferred embodiment, the subject is a human female. 4.4. Pharmaceutical Compositions The pharmaceutical compositions according to the present invention preferably comprise one or more pharmaceutically acceptable carriers and the active constituents. The carrier(s) must be "acceptable" in the sense of being compatible with the other ingredients of the composition and not deleterious to the recipient thereof.

It will be appreciated that the amounts of phytochemical required for said treatment will vary according to the route of administration, the disorder to be treated, the condition, age, and file history of the subject, the galenic formulation of the pharmaceutical composition, etc.

Preferably, the phytochemical used in the invention has been processed to enhance bioavailability, as is described in U.S. Pat. No. 6,086,915. So processed DIM or LTr-1 is referred to as "processed DIM" and "processed LTr-1", respectively. However, any suitable preparation of phytochemical can be used in the methods and compositions of the invention.

The following is a list of ingredients useful for formulating processed DIM or LTr-1:

1. About 10 to about 40 percent by weight of LTr-1 or DIM.
2. About 10 to about 40 percent by weight of the following, alone or in combination: vitamin E succinate polyethylene glycol 1000; vitamin E succinate Polyethylene glycols with polyethylene glycol (with a molecular weight range of 400-2000); other polyethylene glycol esters such as those formed by fatty acids such as oleic acid or stearic acid; polyvinylpyrrolidones; polyvinylpolypyrrolidones; Poloxamer 188, Tweens; or Spans.
3. About 5 to about 20 percent by weight of the following, alone or in combination: phosphatidyl choline (derived from soy lecithin and supplied as Phospholipon 50G from Rhone Poulenc Rorer); dioleoyl phosphatidylcholine; phoshatidylglycerol; dioleoylphosphatidylglycerol; dimyristoylphosphatidylcholine; dipalmitoylphosphatidylcholine; phosphatidylethalolamines; phosphatidylserines; or sphingomyelins; or other sources of phospholipids as those from purified Milk Fat Globule Membrane; glycerolesters; poly glycerol esters; or ethoxylated castor oil.
4. About 15 to about 30 percent by weight of the following, alone or in combination: hexanol; ethanol; butanol; heptanol; 2-methyl-1-pentanol; various ketone solvents that would be acceptable in foods such as methyl ethyl ketone, acetone and others; propylene glycol; and certain ester solvents such as ethyl acetate.
5. About 20 to about 40 percent by weight of the following, alone or in combination: modified starch such as Capsul™ Starch from National Starch, Inc.; methylcellulose; hydroxypropyl methylcellulose; hydroxyethylcellulose; hydroxypropylethylcellulose; pectin; gum arabic; gelatin; or other polymeric matrix-forming preparation known to those skilled in the art, soluble in water and, suitable for spray drying.
6. About 0.5 to about 35 percent by weight of the following, alone or in combination: aerosil 200; or any other flow enhancing excipient from silica, or related salt, known to those skilled in the art.

The following is a detailed method of formulating processed DIM:

1. 6.75 kg of TPGS is heated just beyond its melting point with constant stirring in a heated vessel ("First vessel").
2. 9.38 kg of hexanol and 9.83 kg of jet milled DIM is added to the first vessel and the mixture stirred to a uniform suspension at 70° C. 1.4 kg of phosphatidyl choline is then added.
3. In a second larger vessel, 185 L of water and 10.7 kg of starch are thoroughly mixed with a Cowles blade. This mixture is neutralized to pH 7 with a small amount of sodium carbonate and then heated to 75° C. and stirred for 1 hour.
4. The contents of the first vessel is added to the starch mixture in the second larger vessel and thoroughly mixed with a homogenizing rotor/stator type mixer at moderate speed for 15 minutes.
5. The mixture from step 4 is spray dried with a small amount (approximately 0.5%) of hydrophilic silica to provide a free flowing powder of finely dispersed microparticles containing the co-precipitated TPGS, phosphatidyl choline and DIM in an amorphous, non-crystalline structure.
6. The flowable powder product is collected and stored in evacuated foil sacks, after de-aerating and flushing with nitrogen.
7. Analysis of presence of unchanged dietary ingredient, reveals about 30 to about 33 percent by weight of DIM.

The procedure of making processed DIM may be summarized as follows:

(a) heating one or more solubilizing emulsifiers selected from the group consisting of vitamin E succinate polyethylene glycol 1000, polyvinylpyrrolidone, polyoxyethylene stearate, sodium cholate, deoxycholate and taurocholate;

(b) adding to the product of step (a) a solvent and a surfactant phospholipid selected from the group consisting of phosphatidyl choline, dioleoyl phosphatidyl choline, phosphatidylglycerol, dioleoylphosphatidylglycerol, dimyristoylphosphatidylcholine, dipalitoylphosphatidylcholine, phosphatidylethanolamine, phosphatidylserine and sphingomyelin to produce a solution;

(c) dissolving in the solution of step (b) LTr-1 and/or DIM;

(d) adding to the solution of step (c) a solution containing an encapsulator;

(e) mixing the solution produced in step (d) to produce a microdispersion with a particle size of 5 microns or less; and (f) spray drying the resulting mixture to leave a solid hydrophobic phytochemical composition.

In general, a suitable (therapeutically effective) amount of I3C is 300-500 mg per day. In general, a suitable (therapeutically effective) amount of DIM or LTR is 100-500 mg per day. DIM is preferably administered in an absorption enhancing formulation, as described in U.S. Pat. No. 6,086,915, at 50-200 mg per day, more preferably 400-800 mg per day, as a suspension of microparticles in a starch carrier matrix. The LTr-1 is preferably administered in an absorption enhancing formulation at 50-200 mg per day, more preferably 200-800 mg per day, as a suspension of microparticles in a starch carrier matrix. The actually administered amounts of phytochemical may be decided by a supervising physician. The phytochemicals of the invention may be administered alone or in combination with one another, and/or with other dietary supplements. The combinations of phytochemicals and supplements can be in the same composition for administering in combination concurrently, or in different compositions for administering concurrently but separately, or sequentially.

Therapeutic formulations include those suitable for parenteral (including intramuscular and intravenous), oral, rectal, intra-vaginal, or intradermal administration, although oral administration is the preferred route. Thus, the pharmaceutical composition may be formulated as tablets, pills, syrups, capsules, suppositories, formulations for transdermal application, formulations for intradermal uses, powders, especially lyophilized powders for reconstitution with a carrier for intravenous administration, etc.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

Therapeutic formulations suitable for oral administration, e.g., tablets and pills, may be obtained by compression or molding, optionally with one or more accessory ingredients. Compressed tablets may be prepared by mixing phytochemicals, and compressing this mixture in a suitable apparatus into tablets having a suitable size. Prior to the mixing, the phytochemical may be mixed with a binder, a lubricant, an inert diluent and/or a disintegrating agent.

In a preferred embodiment, phytochemical is mixed with a binder, such as microcrystalline cellulose, and a surfactant, such as sodium lauryl sulphate until a homogeneous mixture is obtained. Subsequently, another binder, such as polyvidone, is transferred to the mixture under stirring with a small amount of added water. This mixture is passed through granulating sieves and dried by desiccation before compression into tablets in a standard tableting apparatus.

A tablet may be coated or uncoated. An uncoated tablet may be scored. A coated tablet may be coated with sugar, shellac, film or other enteric coating agents.

Therapeutic formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soybean oil, mineral oil, sesame oil and the like. Formulations for parenteral administration also include a lyophilized powder comprising phytochemical that is to be reconstituted by dissolving in a pharmaceutically acceptable carrier that dissolves said phytochemical.

When the pharmaceutical composition is a capsule, it may contain a liquid carrier, such as a fatty oil, e.g., cacao butter.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides.

In yet another embodiment, the therapeutic compound can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105).

Other controlled release systems are discussed in the review by Langer (1990, Science 249:1527-1533).

In one embodiment of the pharmaceutical composition according to the invention, two or more active constituents are comprised as separate entities. The two entities may be administered simultaneously or sequentially.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The invention is further explained by the following illustrative examples.

5. EXAMPLE 1

Manufacture of Processed DIM or LTr-1 for Enhanced Oral Bioavailability

Preparation of processed DIM and LTr-1 was accomplished according to the steps outlined in U.S. Pat. No. 6,086,915. Briefly, this included mixture of about 10-40% by final weight of either DIM or LTr-1 with about 10-40% by final weight of vitamin E succinate polyethylene glycol 1000 (Vitamin-E-TPGS, Eastman Chemical), 2-20% by final weight, phosphatidyl choline (Phospholipon 50G, Rhone Poulenc) and 15-30% by final weight hexanol. This mixture was made homogeneous by mixing. The homogeneous mixture of indoles and other oil soluble substituents listed above was added to a solution of modified starch in water (Capsul Starch from National Starch, Inc.). The starch component forms form from 30-70% of the final dry weight of the product. The well dispersed final combined mixture was then subjected to spray drying. The resultant product was a fine powder containing either DIM or LTR-1 microparticles contained within the larger starch particles.

6. EXAMPLE 2

Manufacture of Capsules Containing I3C, DIM AND LTr-1

Pure Indole-3-carbinol (I3C) was obtained from standard suppliers (Sabinsa, Inc or Designed Nutritional Products, Inc.). Capsules containing 300-500 mg were manufactured by placing that amount of I3C into opaque gelatin capsules. Capsules containing 150-300 mg of processed DIM, as produced according to the steps described in Example 1, were made by mixing the processed DIM with microcrystaline cellulose and placing the mixed powder into opaque gelatin capsules. In a preferred embodiment, capsules containing 150-300 mg of processed DIM, as produced according to the steps described in Example 1, were made by mixing the processed DIM with microcrystaline cellulose and calcium carbonate and placing the mixed powder into opaque gelatin capsules. Alternatively, pure diindolylmethane (DIM) was obtained from standard suppliers (Sabinsa, Inc or Designed Nutritional Products, Inc.). Capsules containing 300-500 mg were manufactured by placing that amount of DIM into opaque gelatin capsules.

Similarly, capsules containing 150-300 mg of processed LTr-1, as produced according to the steps described in Example 1, were made by mixing the processed LTr-1 with microcrystaline cellulose and placing the mixed powder into opaque gelatin capsules. In a preferred embodiment, capsules containing 150-300 mg of processed LTr-1, as produced according to the steps described in Example 1, were made by mixing the processed LTr-1 with microcrystaline cellulose and calcium carbonate and placing the mixed powder into opaque gelatin capsules.

7. EXAMPLE 3

Manufacture of DIM or LTr-1 in a Cream for Transdermal Delivery

For the aqueous phase of the emulsion, a mixture of 70 grams of propylene glycol and 633 grams of water is heated to 95° C. The oil phase of the emulsion is prepared by heating a mixture of the following to 105° C.: 30 grams cetostearyl alcohol (Alfol 16/18, Vista), 30 grams hydrogenated soy monoglyceride (Myverol 18-06, Quest), 30 g of a mixture of polyoxyethylene stearic acid ester and mono- and di-glycerides of fatty acids (Arlacel 165, ICI), 10 grams polyethylene (Epolene N-34, Eastman), and 50 g of squalene. The active ingredient phase is prepared separately also by gently heating to about 63° C. a mixture of the following to uniformity: 30 g d-α-tocopherol polyethylene glycol 1000 succinate (Vitamin E TPGS, Eastman), 50 g isopropyl myristate, and 15 g of DIM or 15 g of LTr-1. The above oil phase is added to the aqueous phase using a rotor/stator type homogenizer at moderate speed. The mixture is cooled to 75° C. and 50 grams of lemon oil is added with low speed mixing followed by addition of the active ingredient phase. Lastly, 2 g of a 3:1 mixture of methyl paraben to propyl paraben is added to the emulsion. This mixture is transferred to the reservoir of a high pressure homogenizer such as the Microfluidics™ Model 110Y. The emulsion is passed through the homogenizer approximately five times at 15,000 psi operating pressure that is sufficient to form a cream of the desired consistency which will not separate on standing.

For the aqueous phase of the emulsion, a mixture of 70 grams of propylene glycol and 633 grams of water is heated to 95° C. The oil phase of the emulsion is prepared by heating a mixture of the following to 105° C.: 30 grams cetostearyl alcohol (Alfol 16/18, Vista), 30 grams hydrogenated soy monoglyceride (Myverol 18-06, Quest), 30 g of a mixture of polyoxyethylene stearic acid ester and mono- and di-glycerides of fatty acids (Arlacel 165, ICI), 10 grams polyethylene (Epolene N-34, Eastman), and 50 g. of squalene. The active ingredient phase is prepared separately also by gently heating to about 63° C. a mixture of the following to uniformity: 30 g d-α-tocopherol polyethylene glycol 1000 succinate (Vitamin E TPGS, Eastman), 50 g isopropyl myristate, and 15 g of DIM or 15 g of LTr-1. The above oil phase is added to the aqueous phase using a rotor/stator type homogenizer at moderate speed. The mixture is cooled to 75° C. and 50 grams of lemon oil is added with low speed mixing followed by addition of the active ingredient phase. Lastly, 2 g of a 3:1 mixture of methyl paraben to propyl paraben is added to the emulsion. This mixture is transferred to the reservoir of a high pressure homogenizer such as the Microfluidics™ Model 110Y. The emulsion is passed through the homogenizer approximately five times at 15,000 psi operating pressure that is sufficient to form a cream of the desired consistency which will not separate on standing.

8. EXAMPLE 4

Manufacture of DIM or LTr-1 in a Liposomal Spray for Sublingual and Mucosal Delivery A standard liposomal preparation technique was used to prepare a liposomal suspension of DIM and separately, a liposomal preparation of LTr-1. Briefly, propylene glycol (7.0 gms) was heated to 92° C. on a water bath, 8 grams of partially hydrogenated pure egg yolk lecithin, and 320 mg of stearylamine were added and dissolved to give a clear liquid. To this liquid was added 500 mg of jet milled DIM. This translucent solution was added to 200 ml of a 1% aqueous solution of dextran T 40 pre-warmed to 55° C. and the mixture was stirred in a propeller mixer at 50° C. for 3 minutes after which it was cooled to room temperature. This procedure yielded an off-white, dextran T 40/liposome suspension, thus encapsulating the DIM.

Equivalent steps were undertaken to prepare a lipsomal suspension encapsulating LTr-1.

9. EXAMPLE 5

Use of Processed DIM for Treatment of Mastalgia

The purpose of this study was to determine whether dietary supplementation with the cruicferous phytochemical, Diindolylmethane (DIM) is effective in relieving the pain of this chronic condition.

B. R. is a 44 year old woman referred for evaluation of perimenopausal symptoms of chronic recurring breast pain. She had been troubled by breast pain for many years with recent worsening in her symptoms.

At age 35 she had undergone a vaginal hysterectomy due to excessive and painful menstrual periods. Since her ovaries were left intact, she has received no Hormonal Replacement Therapy (HRT). During the last 4 years she experienced a monthly cycle of breast pain for about one week of each month. The breast pain was bilateral, associated with significant tenderness to touch, and a discomfort described as "heaviness or swelling." A trial of a women's health supplement containing Don Quai provided no relief.

Evaluation included a baseline morning urine sample and close assessment of her symptoms of breast pain during the ensuing month. Following this, bioavailable DIM was begun as a supplement at 225 mg per day together with increased dietary fiber. Complete resolution of the breast pain was noted following one month. A second urine sample was obtained after one month on the DIM supplement.

The urine samples were subsequently analyzed for their levels of 2-hydroxy and 16-hydroxy estrogen metabolites, using an Elisa based assay (Estratest, Immunacare, Inc., Bethlehem, Pa.). These results of before and after DIM supplementation breast pain scores and estrogen metabolite testing are summarized below.

| Indicator Monitored | Before DIM | After DIM |
|---|---|---|
| Typical Breast Pain Score<br>KEY: 0 = none<br>1 = mild; 2 = moderate;<br>3 = significant; 4 = severe | Moderate<br>2/4 | Absent<br>0/4 |
| Typical Breast Soreness Score | Significant<br>3/4 | Absent<br>0/4 |
| Urinary Estrogen Metabolites<br>(ng/ml/mg Creatinine): | | |
| 2-Hydroxy estrone level | 22.2 | 26.4 |
| 16-Hydroxy estrone level | 7.3 | 5.1 |
| 2-Hydroxy to 16-Hyroxy estrone ratio | 2.97 | 5.08 |
| Total urinary estrone metabolites | 28.9 | 31.3 |

10. EXAMPLE 6

Open Label Study of Oral Processed DIM in Women With Breast Pain (Mastalgia)

20 women were referred by collaborating physicians for participation in an open label study of the use of a processed DIM dietary supplementation for recurrent mastalgia. Individuals were selected who met the criteria of recurrent bilateral breast pain for at least 6 months. During the study, the participants avoided herbs and other dietary supplements which might effect estrogen. This included avoidance of Evening Primrose Oil, borage oil, soy isoflavones, Red Clover extract, Don Quai, and Black Cohash. Using a breast pain calendar, participating individuals identified their level of pain, soreness, and swelling on separate analog pain scale scores for each category. 18 out of 20 participants showed some improvement in their symptoms which was noted from 10 days to 1 month after initiating supplementation. Of those participants showing improvement, 12 showed significant improvement with levels dropping from moderate and severe to mild or absent. These improvements in symptoms were seen at a dose of 150 to 300 mg/day of the supplement which corresponds to a daily dose of 50-100 mg/day of DIM. No participants reported side effects. Of further note was one participant aged 51 who had complete resolution of pain and noted the disappearance of a breast cyst previously documented by her physician.

11. EXAMPLE 7

Transdermal Use of DIM for Treatment of Chronic Breast Pain

E. B. is a 38 year old woman with the recurrent symptoms of bilateral painful breasts. She describes the pain as bilateral, worse before menstrual periods and occurring every month beginning about 1 week following cessation of her menses. The pain is described as a soreness associated with movement and a feeling of heaviness or swelling of both breasts.

After maintaining a diary documenting breast pain for one menstrual cycle, E. B. began to apply a cosmetic formulation containing DIM. After only one week of application of 5 cc of the cream nightly, complete resolution of the pain was noted. Also noted was a clear resolution in the sense of swelling of the breasts. The cream was used consistently for 2 months and resolution of the pain was documented on a breast pain diary. No side effects were experienced.

Following these two months, use of the cream was discontinued. Within one month, the breast pain recurred although to a lesser severity than was documented before treatment.

12. EXAMPLE 8

The Use of DIM for Endometriosis

P. M. is a slender and athletic woman of 32 years who sought alternatives in her management of severe endometriosis. Her symptoms of recurrent mid-cycle and menstrually associated pain have been diagnosed as due to endometriosis based on pelvic laparoscopy. This procedure confirmed aggressive endometriosis with ectopic endometrial implants removed from the pelvis and associated with intestinal serosal spread. A history of 2 years of intense pelvic pain at mid-cycle and during menstrual flow was reported prior to the laparoscopy. Her mother gives a history of painful menstrual periods starting in her 20's. She went on to develop ovarian cancer requiring radical surgery at 56 years. A maternal aunt developed cervical cancer requiring surgery. Both mother and aunt had a peri-menopausal history of chronic, recurrent breast pain with fibrocystic changes. Like the patient, a younger sister has been troubled with painful menstrual periods and pelvic pain leading to laparoscopy and the diagnosis of endometriosis.

Following the patient's laparoscopy, one menstrual period was still associated with significant pain. Supplementation with bioavailable processed DIM was begun approximately 6 weeks following the laparoscopy. Initial supplementation with bioavailable processed DIM provided 300 mg/day for one month which was reduced to 150 mg/day thereafter. Since starting treatment, there was disappearance of pain at midcycle and improvement of pain associated with menses. The patient continued DIM supplementation for about one year. During this time regular menstrual periods became more comfortable, no longer requiring analgesics. No side effects were reported.

Diagnosis of the endometriosis and reduction in pain severity correlated with serial levels of serum Ca-125 antigen. Ca-125 is a serum marker with documented usefulness in monitoring the activity of endometriosis in a given patient (Pittaway D E and Fayez J A, 1986, "The use of CA-125 in the diagnosis and management of endometriosis", Fertil Steril 46:790). The following chart shows the association of this marker, useful as a measure of changes in the activity of endometriosis.

| Patient Status | Pre Surgery | Post Surgery | Follow-up Visit #1 | Follow-up Visit #2 | Follow up Visit #3 |
|---|---|---|---|---|---|
| Use of DIM | NO | NO | YES | YES | YES |
| Ca-125 Antigen | 69.6 | 54.1 | 26.4 | 23.2 | 34.0 |
| Pain Level | Severe | Moderate | Improved | Improved | Improved |

13. EXAMPLE 9

Use of Transdermal and Processed DIM for the Therapy of Mastalgia With Associated Improvement in Cervical Dysplasia V. H. is a 45 year old woman with a long history of fibrocystic breasts, recurrent severe breast pain, and cervical dysplasia. The breast pain occurs on a monthly basis during the second half of the menstrual cycle and requires the use of analgesics like ibuprofen. The breast pain diminishes with onset of the menses. Abnormal pap smears of the uterine cervix were first noted in her mid thirties. The cervical dysplasia was categorized as Class I cervical intraepithelial neoplasia on a cervical biopsy taken approximately 1 year ago. V. H. began testing transdermal DIM in a 1.5% strength breast cream for relief of monthly breast pain. Dramatic resolution occurred over a period of 2 weeks. During this time, a reduction and disappearance of chronic vaginal discharge which had been present and attributed to the cervical dysplasia were also noted. Following two weeks of transdermal use of DIM, V. H. began daily use of oral processed DIM at a dose of 50 mg per day of DIM. After two months of oral therapy, follow up pelvic examination revealed a more normal appearing cervix. No side effects were noted with the use of either DIM preparation.

What is claimed is:

1. A method of treating cervical dysplasia in a subject having cervical dysplasia comprising administering to the subject an amount of an indole selected from the group consisting of 3,3'-Diindolylmethane (DIM) and 2-(lndol-3-ylmethyl)-3,3'-Diindolylmethane (LTr-1) effective to reduce one or more symptoms associated with cervical dysplasia, wherein the indole is formulated as a tablet, pill, capsule, suppository, cream, parenteral suspension or liposomal spray, or is suspended as microparticles in a starch carrier matrix.

2. The method of claim 1, wherein the indole is DIM.

3. The method of claim 2, wherein the DIM is suspended as microparticles in a starch carrier matrix.

4. The method of claim 1, wherein the subject is a human female.

5. The method of claim 1, wherein the indole is LTr-1.

6. The method of claim 1, wherein the indole is formulated as a tablet.

7. The method of claim 1, wherein the indole is formulated as a pill.

8. The method of claim 1, wherein the indole is formulated as a capsule.

9. The method of claim 1, wherein the indole is formulated as a suppository.

10. The method of claim 1, wherein the indole is formulated as a cream.

11. The method of claim 1, wherein the indole is formulated as a parenteral suspension.

12. The method of claim 1, wherein the indole is formulated as a liposomal spray.

13. The method of claim 1, wherein the indole is suspended as microparticles in a starch carrier matrix.

14. The method of claim 6, 7 or 8, wherein the indole is administered orally.

15. The method of claim 9, 10 or 12, wherein the indole is administered by direct application to the vaginal or cervical mucosa of the subject.

16. The method of claim 9, 10 or 12, wherein the indole is administered transdermally.

\* \* \* \* \*